United States Patent
Osawa (10) Patent No.: US 9,423,238 B2
(45) Date of Patent: Aug. 23, 2016

(54) OPTICAL MEASUREMENT APPARATUS FOR MEASURING A TARGET USING SIGNAL, REFERENCE, AND CONTROL BEAMS

(71) Applicant: Hitachi-LG Data Storage, Inc., Tokyo (JP)

(72) Inventor: Kentaro Osawa, Tokyo (JP)

(73) Assignee: HITACHI-LG DATA STORAGE, INC., Tokyo (JP)

( * ) Notice: Subject to any disclaimer, the term of this patent is extended or adjusted under 35 U.S.C. 154(b) by 21 days.

(21) Appl. No.: 14/503,560

(22) Filed: Oct. 1, 2014

(65) Prior Publication Data

US 2015/0092196 A1 Apr. 2, 2015

(30) Foreign Application Priority Data

Oct. 2, 2013 (JP) .................. 2013-206962

(51) Int. Cl.
*G01B 9/02* (2006.01)
*A61B 5/00* (2006.01)

(52) U.S. Cl.
CPC ......... *G01B 9/02091* (2013.01); *A61B 5/0066* (2013.01); *G01B 9/02025* (2013.01); *G01B 9/02059* (2013.01); *G01B 9/02081* (2013.01); *G01B 2290/70* (2013.01)

(58) Field of Classification Search
CPC .......... G01B 9/02091; G01B 9/02075; G01B 9/02027; G01B 9/02025; G01B 9/02059; G01B 9/02081; G01B 2290/70; A61B 3/102; A61B 5/0033; A61B 5/0073; A61B 2019/5234; G02B 21/0092; G02B 21/0056; G02B 21/006
See application file for complete search history.

(56) References Cited

U.S. PATENT DOCUMENTS

| 2002/0060958 A1* | 5/2002 | Ando | G11B 7/0903 369/44.23 |
| 2004/0100636 A1* | 5/2004 | Somekh | G01N 21/6458 356/497 |
| 2006/0097205 A1* | 5/2006 | Kakuchi | G03F 7/706 250/548 |

(Continued)

FOREIGN PATENT DOCUMENTS

JP 2011-218155 A 11/2011

OTHER PUBLICATIONS

Labiau, S et al., Defocus test and defocus correction in full-field optical coherence tomgoraphy, May 13, 2009, Optics letters, vol. 34, No. 10, pp. 1576-1578.*

(Continued)

*Primary Examiner* — Michael P Lapage
(74) *Attorney, Agent, or Firm* — Baker Botts L.L.P.

(57) ABSTRACT

A clear image of a target to be measured is obtained by suppressing influence of a reflected beam from the surface of the target or a measurement target holding unit. A laser beam emitted from a light source is split into a signal beam, reference beam, and control beam. The signal beam is focused onto the target with an objective lens, so the target is irradiated with the signal beam. The amount of defocus of the control beam is controlled with a defocus control unit, and the phase of the control beam is controlled with a phase control unit. A signal beam reflected or scattered by the target is combined with the control beam to generate a controlled signal beam, and the controlled signal beam is combined with the reference beam. A plurality of interference beams with different phases are generated with interference optics, and phase diversity detection is performed.

16 Claims, 6 Drawing Sheets

(56) References Cited

U.S. PATENT DOCUMENTS

2011/0317259 A1* 12/2011 Tanabe .................. G02B 21/06
359/383
2012/0300217 A1    11/2012 Yuasa
2014/0218684 A1*  8/2014 Kumar ............... G01N 21/4795
351/206

OTHER PUBLICATIONS

Toyohiko Yamauchi et al., Label-free imaging of intracellular motility by low-coherent quantitative phase microscopy, Optics Express, Mar. 14, 2011, pp. 5536-5550, vol. 19, No. 6.

* cited by examiner

OPTICAL MEASUREMENT APPARATUS FOR MEASURING A TARGET USING SIGNAL, REFERENCE, AND CONTROL BEAMS

CLAIM OF PRIORITY

The present application claims priority from Japanese patent application JP 2013-206962 filed on Oct. 2, 2013, the content of which is hereby incorporated by reference into this application.

TECHNICAL FIELD

The present invention relates to an optical measurement apparatus, and more particularly to an optical measurement apparatus for optically observing cross-sections.

RELATED ART

In recent years, optical coherence tomography (OCT) has been drawing attention that acquires an image reflecting the surface structure or the inner structure of a target to be measured, using a light beam (See Patent Document 1). As the OCT is not invasive on the human body, it is expected to be applied to the medical field and the biological field, in particular. In the ophthalmological field, apparatuses for forming images of fundus oculi or corneas have been put into practical use. In the OCT, a light beam from a light source is split into two: a signal beam to irradiate a target to be measured, and a reference beam to be reflected by a reference beam mirror without irradiating the target to be measured, and then, a signal beam reflected from the target to be measured is combined with and thus is caused to interfere with the reference beam, whereby an interference signal is obtained.

The OCT is broadly divided into the time domain OCT and the Fourier domain OCT depending on the method of moving a measurement position in the optical axis direction (hereinafter referred to as z-scan). In the time domain OCT, z-scan is performed by using a low coherence light source as a light source and moving a reference beam mirror during the measurement. Accordingly, only the components in a signal beam that have the same optical path lengths as the reference beam will interfere with the reference beam, whereby an interference signal is obtained. When envelope detection is performed on the interference signal, a desired signal is obtained through demodulation. Meanwhile, the Fourier domain OCT is further divided into the wavelength-scanning OCT and the spectral domain OCT. In the wavelength-scanning OCT, z-scan is performed by using a wavelength-scanning light source capable of causing the wavelength of an emitted beam to scan, and causing the wavelength to scan during the measurement. When Fourier transform is performed on the wavelength dependence of the detected interference beam intensity (i.e., an interference spectrum), a desired signal is obtained through demodulation. In the spectrum domain OCT, the following corresponds to the z-scan: using a broadband light source for a light source, splitting a generated interference beam using a beam splitter, and detecting the interference beam intensity (i.e., an interference spectrum) for each wavelength component. When Fourier transform is performed on the obtained interference spectrum, a desired signal is obtained through demodulation.

PRIOR ART DOCUMENTS

Patent Document 1: JP 2011-218155 A
Non-patent Document 1: Optics Express Vol. 19, 5536-5550 (2011)

SUMMARY OF THE INVENTION

Problems to be Solved by the Invention

Figure 1:
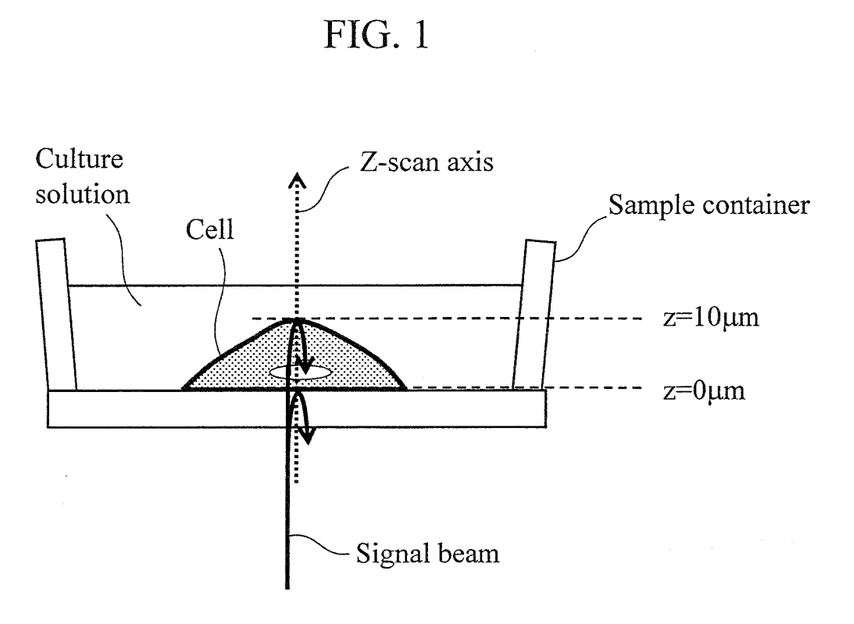
FIG. 1 is a schematic view showing an example of a target to be measured with the conventional OCT apparatus and the OCT apparatus of the present invention.
Figure 2:
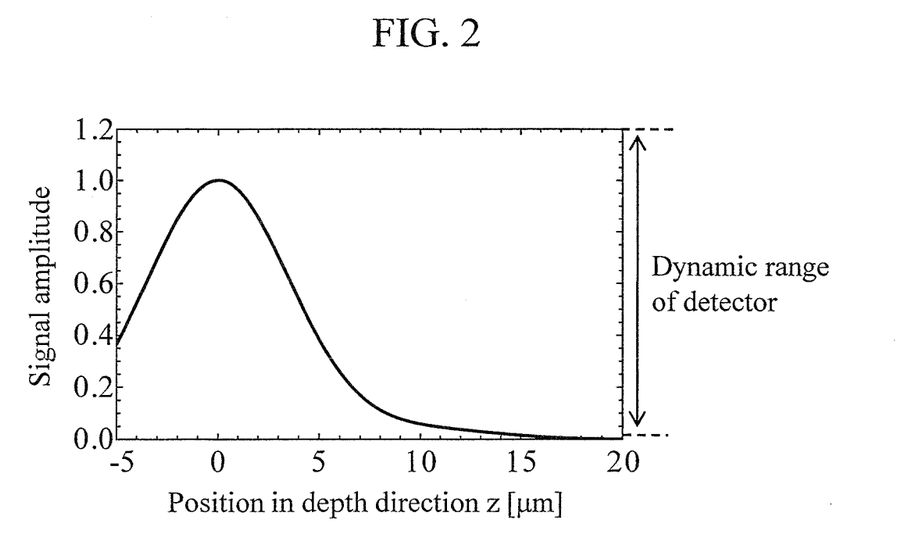
FIG. 2 is a schematic view showing an example of a signal measured with the conventional OCT apparatus.

When a living organism is measured with the OCT, a reflected beam from the inside of a target to be measured is typically far weaker than a reflected beam from the surface of the target to be measured or a reflected beam from the interface between a measurement target holding portion, such as cover glass or a cell culture vessel, and the target to be measured. For example, suppose a case where a cell in a culture vessel, which is filled with a culture solution, is measured as shown in FIG. 1. The refractive index of a typical culture vessel (made of polystyrene) is about 1.59, and the refractive index of the cell is about 1.37. From such values, the reflectivity of the interface between the culture vessel and the cell is estimated to be about 0.55%. Meanwhile, provided that the refractive index of the culture solution is about 1.33, the reflectivity of the interface between the cell and the culture solution is about 0.022%. The reflectivity of the interface between different cells or the inside of a cell is considered to be even smaller than 0.022%. FIG. 2 shows an example of a waveform when a signal is acquired along the z-scan axis shown in FIG. 1, using an OCT apparatus with a resolution in the optical-axis direction of 5 μm. Herein, two reflecting points (i.e., the bottom surface of the culture vessel and the apex of the cell) are away from each other by 10 μm when calculated in terms of the optical path length. FIG. 2 can confirm that the amplitude of a peak that corresponds to the bottom surface of the culture vessel is extremely large, which makes a signal from the apex of the cell unnoticeable, and thus makes the signal difficult to identify.

As described above, as the conventional OCT apparatus detects a strong reflected beam from the surface of the target to be measured or from the interface between the measurement target holding portion and the target to be measured, there is a problem in that it is impossible to clearly visualize the structure of the target to be measured around a region from which the strong reflected beam is generated.

Solution to the Problems

In order to solve the aforementioned problem, the present invention splits a laser beam emitted from a light source into a signal beam, a reference beam, and a control beam; focuses the signal beam onto a target to be measured with an objective lens so as to irradiate the target with the signal beam; combines a signal beam reflected or scattered by the target to be measured with the control beam, thereby generating a controlled signal beam; combines the controlled signal beam with the reference beam to generate a plurality of interference beams with different phases; and detects the interference beams. A focus position of the signal beam is moved by a focus position moving unit. In addition, defocus of the control beam is controlled such that the amount of defocus of the control beam becomes equal to that of a beam, which is contained in the signal beam, reflected by the surface of the target to be measured or by a measurement target holding unit. The phase of the control beam is controlled such that it is different from the phase of the signal beam by 180°.

Accordingly, control beam components and reflected beam components from the surface of the target to be measured or from the measurement target holding unit are cancelled out against each other, so that the surface of the target to be measured or the structure of the target to be measured around the measurement target holding unit can be clearly visualized.

As an example, the numerical aperture of the objective lens that focuses a signal beam onto the target to be measured is greater than or equal to 0.4.

Accordingly, it is possible to achieve a spatial resolution in the optical axis direction that is greater than or equal to that of the conventional OCT apparatus without using a wideband light source or a wavelength scanning light source.

As an example, a spherical aberration imparting unit configured to impart a spherical aberration to the control beam is provided.

Accordingly, the efficiency of interference between the control beam and the reflected beam from the surface of the target to be measured or from the measurement target holding unit improves. Thus, contribution of a reflected beam from the surface of the target to be measured or from the measurement target holding unit can be suppressed more.

As an example, the amount of defocus of the control beam is controlled so that the difference between the amount of defocus of the control beam and the amount of defocus of a beam, which is contained in the signal beam, reflected by the surface of the target to be measured or by a holding unit that holds the target to be measured is $0.856\lambda/(NA)^2$ where the wavelength of the laser beam is $\lambda$ and the numerical aperture of the objective lens is NA.

Accordingly, the efficiency of interference between the control beam and the reflected beam from the surface of the target to be measured or from the measurement target holding unit improves. Thus, contribution of a reflected beam from the surface of the target to be measured or from the measurement target holding unit can be suppressed more.

As an example, the laser beam is split into two, and a beam reflected by a flat plate, which is inserted in the optical path of one of the split laser beams and is substantially transparent to a laser beam, is used as a control beam, and defocus of the control beam is controlled by controlling the position of the transparent flat plate in the optical axis direction.

Accordingly, it is possible with a simple and compact optical configuration to allow control beam components and reflected beam components from the surface of the target to be measured or from the measurement target holding unit to be cancelled out against each other, and thus clearly visualize the surface of the target to be measured or the structure or the target to be measured around the measurement target holding unit.

As an example, the interference optics are configured to generate four interference beams. An interference phase of the signal beam and the reference beam of each of the four interference beams differs from one another by an integral multiple of substantially 90°. Pairs of interference beams are detected by a current differential detector, each pair having a difference of substantially 180° in the interference phase of the signal beam and the reference beam. Then, the sum of squares of the two obtained detection signals is determined, for example.

Accordingly, a stable signal that has no dependence on the phase difference between a signal beam and a reference beam and is proportional to the intensity of the signal beam can be obtained. In addition, it is also possible to, by determining the ratio between the two obtained detection signals and performing arc tangent thereon, acquire phase information on the signal beam. Further, as a current differential detector is used, the detector will not easily be saturated even when the intensity of the reference beam is increased. Thus, the S/N ratio of the signal can be increased than when the current differential detector is not used.

As an example, the optical path length difference between the signal beam and the reference beam is modulated by an optical path length modulating unit more rapidly than the rate of change of the optical path length of the signal beam that occurs while the focus position of the signal beam is moved, and the interference optics are configured to generate two interference beams. The two interference beams are detected by a current differential photodetector, and envelope detection is performed on the detection signals.

Accordingly, a desired signal can be acquired with less detectors.

Effect of the Invention

According to the present invention, an optical measurement apparatus can be provided that can suppress influence of a reflected beam from the surface of a target to be measured or from a measurement target holding portion, and thus can visualize the surface of the target to be measured or the structure of the target to be measured around the measurement target holding portion.

Other problems, configurations, and advantages will become apparent from the following description of embodiments.

MODE FOR CARRYING OUT THE INVENTION

Hereinafter, embodiments of the present invention will be described with reference to the drawings.

[Embodiment 1]

Figure 3:
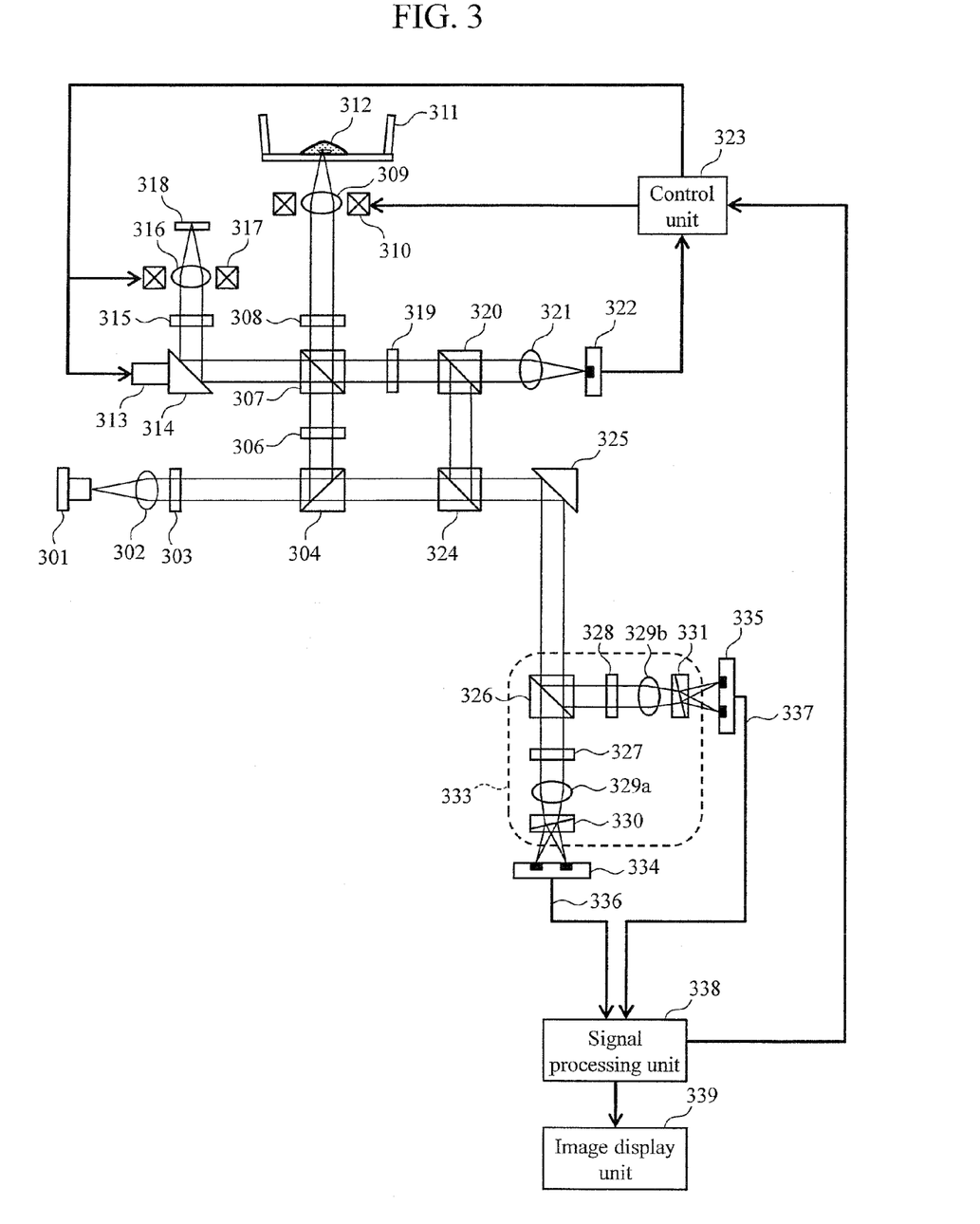
FIG. 3 is a schematic view showing an exemplary configuration of the optical measurement apparatus of the present invention.

FIG. 3 is a schematic view showing the basic embodiment of the optical measurement apparatus of the present invention.

A laser beam is emitted from a light source 301. The laser beam is converted into a collimated beam by a collimator lens 302, and is subjected to polarization rotation by a λ/2 plate 303 capable of adjusting the optical axis direction, and is further split into two by a polarization beam splitter 304. One of the light beams split by the polarization beam splitter 304 becomes incident on a polarization beam splitter 324 as a reference beam. The other of the light beams split by the polarization beam splitter 304 is subjected to polarization rotation by a λ/2 plate 306 capable of adjusting the optical axis direction, and is then split into two: a signal beam and a control beam by a polarization beam splitter 307.

The signal beam passes through a λ/4 plate 308 at which the optical axis is set to about 22.5° with respect to the horizontal direction, and thus is converted from the p-polarized beam into a circularly polarized beam. Then, the beam is focused onto a target 312 to be measured, which is arranged in a sample container 311, by an objective lens 309 with a numerical aperture of greater than or equal to 0.4, so as to irradiate the target 312 to be measured. Herein, the objective lens 309 is moved by an objective lens actuator 310 under the control of a control unit 323, so that the focus position (i.e., measurement position) of the signal beam is moved by the objective lens 309. A signal beam reflected or scattered by the target to be measured passes through the objective lens 309 again, and is then converted from the circularly polarized beam into a s-polarized beam by the λ/4 plate 308. Then, the beam becomes incident on the polarization beam splitter 307.

The control beam is reflected by a mirror 314 attached to a piezoelectric element 313. Then, the control beam passes through a λ/4 plate 315 at which the optical axis is set to about 22.5° with respect to the horizontal direction, and thus is converted from the s-polarized beam into a circularly polarized beam. Then, the control beam irradiates a flat plate 318, which has a reflective film deposited on its rear surface, by an objective lens 316 that is the same lens as the objective lens 309. The control beam reflected by the flat plate 318 passes through the objective lens 316 again. Then, the control beam is converted from the circularly polarized beam into a p-polarized beam by the λ/4 plate 315, and then becomes incident on the polarization beam splitter 307. Herein, the thickness and material of the flat plate 318 are set so that spherical aberrations that are imparted to the control beam by the flat plate 318 become equal to spherical aberrations that are imparted to the reflected beam from the sample container 311 by the sample container. As the flat plate 318, the same container as the sample container 311 can be used, for example.

The control beam and the signal beam are combined by the polarization beam splitter 307. Then, the combined beam is subjected to polarization rotation by a λ/2 plate 319 capable of adjusting the optical axis direction, and is then split into two by a polarization beam splitter 320. One of the light beams split by the polarization beam splitter 320 is focused by a condenser lens 321 and is then detected by a detector 322. The other of the light beams split by the polarization beam splitter 320 becomes incident on the polarization beam splitter 324 as a controlled signal beam.

Herein, the phase of the control beam is controlled by driving the piezoelectric element 313 with the control unit 323 such that the intensity of a light beam detected by the detector 322 becomes maximum. In addition, defocus of the control beam is controlled by driving an objective lens actuator 317 with the control unit 323 such that the amount of defocus of the control beam becomes equal to that of a reflected beam from the bottom surface of the sample container 311 (to be more precise, the interface between the sample container 311 and the target 312 to be measured) contained in the signal beam.

The controlled signal beam and the reference beam are combined by the polarization beam splitter 324, whereby a combined beam is generated. The combined beam is reflected by a mirror 325, and is then guided to interference optics 333 that include a half beam splitter 326, a λ/2 plate 327, a λ/4 plate 328, condenser lenses 329a and 329b, and Wollaston prisms 330 and 331.

The combined beam that becomes incident on the interference optics 333 is divided into two: a transmitted beam and a reflected beam by the half beam splitter 326. The transmitted beam passes through the λ/2 plate 327 at which the optical axis is set to about 22.5° with respect to the horizontal direction, and is focused by a condenser lens 329a, and is further split into two by the Wollaston prism 330, whereby a first interference beam and a second interference beam having a phase difference of 180° are generated. The first interference beam and the second interference beam are detected by a current differential photodetector 334, whereby a signal 336 that is proportional to the intensity difference between the first interference beam and the second interference beam is output.

Meanwhile, the reflected beam passes through the λ/4 plate 328 at which the optical axis is set to about 45° with respect to the horizontal direction, and is focused by the condenser lens 329b, and is further split into two by the Wollaston prism 331, whereby a third interference beam and a fourth interference beam having a phase difference of 180° are generated. Herein, the third interference beam has a phase difference of 90° from the first interference beam. The third interference beam and the fourth interference beam are detected by a current differential photodetector 335, whereby a signal 337 that is proportional to the intensity difference between the third interference beam and the fourth interference beam is output. The thus generated signals 336 and 337 are input to a signal processing unit 338 and are operated, whereby a signal that is proportional to the amplitude of the signal beam is obtained. A tomographic image of the target to be measured that is formed on the basis of such signal is displayed on an image display unit 339.

Next, the function of the optics up to when a controlled signal beam is generated will be described. The Jones vector of a signal beam at a time point when the signal beam becomes incident on the polarization beam splitter 307 after being reflected by the target to be measured and the bottom surface of the sample container is represented as follows.

$$\begin{pmatrix} 0 \\ E_{sig} + E_{str} \end{pmatrix} \quad (1)$$

Herein, $E_{sig}$ represents the complex amplitude of signal beam components reflected by the target to be measured (i.e., from the focus position of the objective lens), and $E_{str}$ represents the complex amplitude of signal beam components reflected by the bottom surface of the sample container. Such complex amplitudes typically have different amounts of defocus. In addition, the Jones vector of a control beam at a time point when the control beam becomes incident on the polarization beam splitter 307 after being reflected by the flat plate 318 is represented as follows.

$$\begin{pmatrix} E_{reg} \\ 0 \end{pmatrix} \quad (2)$$

Herein, the phase and the amount of defocus of the control beam $E_{reg}$ are controlled by the piezoelectric element 313 and the objective lens actuator 317. The Jones vector of a light beam, which is generated when the signal beam represented by Formula (1) is combined with the control beam represented by Formula (2) by the polarization beam splitter, is represented by the following formula.

$$\begin{pmatrix} E_{reg} \\ E_{sig} + E_{str} \end{pmatrix} \quad (3)$$

Provided that the angle of the $\lambda/2$ plate 319 in the optical axis direction is $\theta$ degree, the Jones vector of the light beam that has passed through the $\lambda/2$ plate 319 is represented as follows.

$$\begin{pmatrix} \cos(2\theta) & \sin(2\theta) \\ \sin(2\theta) & -\cos(2\theta) \end{pmatrix} \begin{pmatrix} E_{reg} \\ E_{sig} + E_{str} \end{pmatrix} = \quad (4)$$

$$\begin{pmatrix} E_{reg}\cos(2\theta) + (E_{sig} + E_{str})\sin(2\theta) \\ E_{reg}\sin(2\theta) + (E_{sig} + E_{str})\cos(2\theta) \end{pmatrix}$$

Accordingly, a signal $I_{FB}$ that is detected by the detector 322 after having passed through the polarization beam splitter 320 is represented by the following formula.

$$I_{FB} = \frac{1}{2}\int_D |E_{reg}\cos(2\theta) + (E_{sig} + E_{str})\sin(2\theta)|^2 \, dr \quad (5)$$

$$= \int_D \begin{bmatrix} |E_{sig}|^2\sin^2(2\theta) + |E_{str}|^2\sin^2(2\theta) + \\ |E_{reg}|^2\cos^2(2\theta) + \\ |E_{sig}||E_{reg}|\sin(4\theta)\cos(\phi_{sig} - \phi_{reg}) + \\ 2|E_{reg}||E_{str}|\sin(4\theta)\cos(\phi_{reg} - \phi_{str}) - \\ 2|E_{str}||E_{sig}|\sin^2(2\theta)\cos(\phi_{str} - \phi_{sig}) \end{bmatrix} dr$$

Herein, symbol $r=(x,y)$ represents the coordinate vector of the cross-section of the light beam, symbol D represents the detection region, and symbol $\int_D dr$ represents an integration operation in the whole range within the light beam. Symbols $\phi_{sig}$, $\phi_{str}$, and $\phi_{reg}$ represent the wave front of a signal beam reflected by the target to be measured, the wave front of a signal beam reflected by the bottom surface of the sample container, and the wave front of the control beam, respectively, and include phase information and defocus information on the respective beams. As described above, defocus of the control beam is controlled by the objective lens actuator 317 such that the amount of defocus of the control beam is always equal to the amount of defocus of a signal beam reflected by the bottom surface of the sample container. That is, defocus of the control beam is controlled such that components that depend on the square of the absolute value of the space coordinates r of $\phi_{reg}$ becomes equal to that of $\phi^{str}$. The amount of defocus can be controlled by synchronizing the movement of the objective lens 316 in the optical axis direction with the movement of the objective lens 309 in the optical axis direction.

The phase of the control beam is controlled by the piezoelectric element 313 such that $I_{FB}$ represented by Formula (5) becomes maximum. In Formula (5), the values of the fourth and fifth terms will change depending on the phase of the control beam. The fourth term represents the interference between the control beam and the signal beam reflected by the target to be measured, and $|E_{sig}|<<|E_{reg}|$, $|E_{str}|$. Thus, it is smaller than the contribution of the fifth term. Further, as the amount of defocus of the control beam differs from that of the signal components reflected by the target to be measured, a ring-like interference pattern is formed on the detector 322, and such beams will not uniformly strengthen or weaken against each other on the detector 322. Accordingly, the rate of change of the value of the fifth term in response to a change in the phase of the control beam is smaller than that of the fourth term. Thus, phase control of the control beam with the piezoelectric element 313 is performed so as to approximately maximize the fifth term in Formula (5). Thus, as a result of performing defocus control and phase control, it is found that the relationship between the wave front of the control beam and the wave front of the signal beam components from the bottom surface of the sample container satisfies $\phi_{reg}=\phi_{str}$.

Meanwhile, the Jones vector of the controlled signal beam generated by being reflected by the polarization beam splitter 320 can be represented as follows using the relationship of $\phi_{reg}=\phi_{str}$.

$$-\cos(2\theta)\begin{pmatrix} 0 \\ E_{sig} + (|E_{str}| - |E_{reg}|\tan(2\theta))e^{i\phi_{str}} \end{pmatrix} \quad (6)$$

From Formula (6), it is found that by adjusting the intensity of the control beam ($|E_{reg}|^2$) by adjusting the angle of the $\lambda/2$ plate 306 in the optical axis direction or by adjusting the value of $\tan 2\theta$ by adjusting the angle of the $\lambda/2$ plate 319 in the optical axis direction so as to satisfy $|E_{reg}|\tan 2\theta \approx |E_{str}|$, it becomes possible to allow the reflected beam from the sample container and the control beam to be cancelled out against each other. Such adjustment can be easily performed by measuring the reflectivity of the sample container in advance.

The controlled signal beam is combined with the reference beam by the polarization beam splitter 324, and the thus generated combined beam of the controlled signal beam and the reference beam is reflected by the mirror 325, and then becomes incident on the interference optics 333. The Jones vector of the combined beam at a time point when the combined beam becomes incident on the interference optics 333 is represented by:

$$\begin{pmatrix} E_{reg} \\ E'_{sig} \end{pmatrix}, \quad (7)$$

where $E_{ref}$ represents the complex electric field amplitude of the reference beam, and $E'_{sig}$ represents the complex electric field amplitude of the controlled signal beam. When $|E_{reg}|\tan 2\theta \approx |E_{str}|$ is used, $E'_{sig}$ can be approximately represented by the following formula.

$$E'_{sig} = -\cos(2\theta) E_{sig} \quad (8)$$

The Jones vector of a combined beam that has passed through the half beam splitter 326 and has further passed through the λ/2 plate 327 is represented as follows.

$$\begin{pmatrix} 1/\sqrt{2} & -1/\sqrt{2} \\ 1/\sqrt{2} & 1/\sqrt{2} \end{pmatrix} \begin{pmatrix} E_{ref}/\sqrt{2} \\ E'_{sig}/\sqrt{2} \end{pmatrix} = \frac{1}{2}\begin{pmatrix} -E'_{sig} + E_{ref} \\ E'_{sig} + E_{ref} \end{pmatrix} \quad (9)$$

The combined beam represented by Formula (9) is split into two: p-polarized components and s-polarized components by the Wollaston prism 330, which are then differentially detected by the current differential photodetector 334. Thus, the detection signal 336 is represented as follows.

$$I = \int_D \left[\frac{1}{4}|E'_{sig} + E_{ref}|^2 - \frac{1}{4}|-E'_{sig} + E_{ref}|^2\right] dr \quad (10)$$
$$= \int_D |E'_{sig}||E_{ref}|\cos(\phi'_{sig} - \phi_{ref}) dr$$

Herein, $\phi'_{sig}$ and $\phi_{ref}$ represent the phases when the complex numbers $E'_{sig}$ and $E_{ref}$ are represented in polar coordinates, respectively. For the sake of simplicity, the conversion efficiency of the detector is assumed to be 1.

Meanwhile, the Jones vector of the combined beam that has been reflected by the half beam splitter 326 and has further passed through the λ/4 plate 328 is represented as follows.

$$\begin{pmatrix} i/\sqrt{2} & 1/\sqrt{2} \\ 1/\sqrt{2} & i/\sqrt{2} \end{pmatrix} \begin{pmatrix} E'_{sig}/\sqrt{2} \\ E_{ref}/\sqrt{2} \end{pmatrix} = \frac{1}{2}\begin{pmatrix} i(E'_{sig} - iE_{ref}) \\ E'_{sig} + iE_{ref} \end{pmatrix} \quad (11)$$

The combined beam represented by Formula (11) is split into two: p-polarized components and s-polarized components by the Wollaston prism 331, which are then differentially detected by the current differential photodetector 335. Thus, the detection signal 337 is represented as follows.

$$Q = \int_D \left[\frac{1}{4}|E'_{sig} + iE_{ref}|^2 - \frac{1}{4}|E'_{sig} - iE_{ref}|^2\right] dr \quad (12)$$
$$= \int_D |E'_{sig}||E_{ref}|\sin(\phi'_{sig} - \phi_{ref}) dr$$

The above outputs are operated as follows by the signal processing unit 338, whereby a signal that is independent of the phase and is proportional to the intensity of the controlled signal beam is obtained.

$$|E'_{sig}|^2 |E_{ref}|^2 = I^2 + Q^2 \quad (13)$$

As described above, four interference beams each having a phase difference of 90° are generated by the interference optics 333, and are then detected, whereby a signal having no phase dependence is obtained. However, in principle, a similar signal can be obtained as long as the number of the interference beams generated is greater than or equal to three. For example, when three interference beams each having a phase difference of 60° are generated and detected, the same signal as the signal represented by Formula (13) can be obtained.

In this embodiment, a control beam with the controlled defocus and phase is overlaid on a signal beam, whereby a reflected beam from a sample container, which is contained in the signal beam, can be cancelled out.

Figure 4:
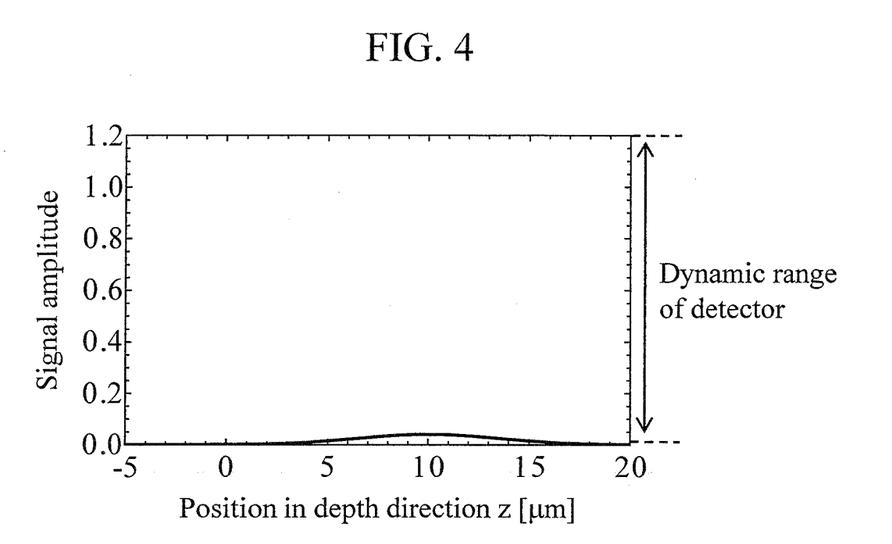
FIG. 4 is a schematic view showing an example of a signal measured with the OCT apparatus of the present invention.
Figure 5:
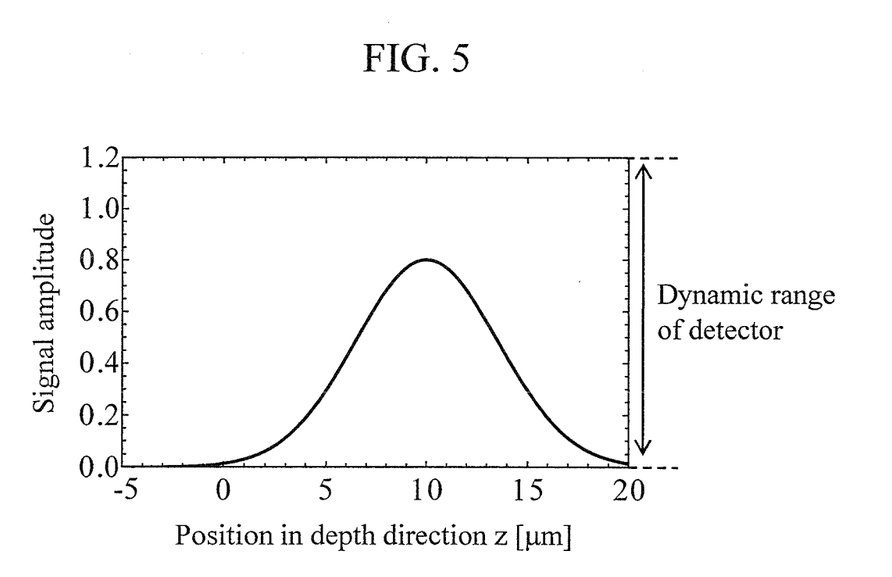
FIG. 5 is a schematic view showing an example of a signal measured with the OCT apparatus of the present invention.

FIGS. 4 and 5 show examples of the results when a reflected signal from the target to be measured shown in FIG. 1 is acquired with the OCT apparatus of this embodiment. Vertical resolution is 5 μm as with the measurement results of the conventional OCT apparatus shown in FIG. 2. FIGS. 4 and 5 each show the measurement results of the OCT apparatus of this embodiment. Specifically, FIG. 5 shows the results when the intensity of the reference beam or the gain of the detector is increased than that of FIG. 4.

In FIG. 4, strong reflection from a sample container is suppressed more than when the conventional OCT apparatus in FIG. 2 is used. Thus, a peak that corresponds to reflection from a cell can be confirmed at a position of z=10 μm. Accordingly, the surface of the target to be measured or the structure of the target to be measured around the measurement target holding unit can be clearly visualized. In addition, as a strong reflected beam from the sample container is suppressed, the detector will not be easily saturated. Thus, it is possible to amplify the signal from the target to be measured as shown in FIG. 5 by increasing the intensity of the reference beam or the gain of the detector. Accordingly, the surface of the target to be measured or the structure of the target to be measured around the measurement target holding unit can be visualized more clearly.

Next, the spatial resolution of the OCT apparatus of the present invention will be described. Herein, spatial resolution in the optical axis direction is defined as the full width at half maximum of a peak, which corresponds to a single reflective plane, obtained when the objective lens is moved in the optical axis direction. A signal that corresponds to Formula (13) when the focus position is deviated from the reflective plane by z is represented by the following formula.

$$sig(z) = |E'_{sig}|^2 |E_{ref}|^2 \mathrm{sinc}^2\left(\pi \cdot \frac{z}{\lambda} NA^2\right) \quad (14)$$

From the above formula, the full width at half maximum of a signal from a single reflective plane, that is, spatial resolution in the optical axis direction can be approximately represented as follows.

$$0.886 \frac{\lambda}{NA^2} \quad (15)$$

Herein, λ represents the wavelength of a laser beam and NA represents the numerical aperture of the objective lens 309. Typically, the wavelength of a light beam used in the OCT apparatus is about 600 to 1300 nm that are difficult to be absorbed by hemoglobin or even by water. For example, provided that the numerical aperture of the objective lens is greater than or equal to 0.4, spatial resolution in the optical axis direction at a wavelength of 600 to 1300 nm is about 3.3 to 7.2 μm. Thus, resolution in the optical axis direction that is greater than or equal to that of the conventional OCT apparatus can be achieved.

In addition, in this embodiment, the thickness of a region of the flat plate 318 through which a light beam passes is set so that spherical aberrations that are imparted to the control beam by the flat plate 318 become equal to spherical aberrations that are imparted to the reflected beam from the sample container 311 by the sample container. Therefore, the efficiency of interference between the control beam and the reflected beam from the sample container improves. Accordingly, the reflected beam from the sample container can be cancelled out more precisely, and thus, the surface of the target to be measured or the structure of the target to be measured around the measurement target holding unit can be visualized more clearly.

In this embodiment, it is also possible to acquire phase information on a signal beam, which is based on the phase of a reference beam, by performing the following operation.

$$\arctan\left(\frac{Q}{I}\right) \quad (16)$$

Examples of the method for using the phase information on a signal beam include imaging of cell activity such as the one described in Non-patent Document 1.

Finally, the required accuracy for the defocus control in the present invention will be described. Provided that the amount of defocus of a control beam and that of a reflected beam from the sample container (i.e., the distance from the focus position of the objective lens to the reflective plane) are $z_{reg}$ and $z_{str}$, respectively, the efficiency of interference between the control beam and the reflected beam from the sample container is represented by the following formula.

$$\mathrm{sinc}\left(\pi \cdot \frac{\Delta z}{\lambda} NA^2\right) \quad (17)$$

Herein, $\Delta z = z_{reg} - z_{str}$. For example, in order to set the contribution of a reflected beam from the sample container to less than or equal to 10% of the conventional apparatus, the value of Formula (17) should be greater than or equal to 0.95. At this time, the permissible amount of deviation $\Delta z$ of the defocus control is represented as follows:

$$\Delta z \leq \phi_0 \frac{\lambda}{\pi NA^2} \quad (18)$$

Herein, $\phi_0$ is a constant that satisfies $\sin \phi_0 = 0.95$, and is about 0.5519. When the value is substituted into Formula (18), the right side of Formula (18) is represented by $0.856\lambda/(NA)^2$, and when $\lambda = 0.780$ μm and $NA = 0.4$, for example, the value of the right side of Formula (18) is 0.86 μm. This is a value that can be realized by controlling the objective lens actuator 317. When the value of Formula (17) is greater than or equal to 0.95, the contribution of a reflected beam from the sample container becomes less than or equal to 10% of the conventional apparatus. Thus, the surface of the target to be measured or the structure of the target to be measured around the measurement target holding unit can be visualized more clearly than with the conventional apparatus.

[Embodiment 2]

Figure 6:
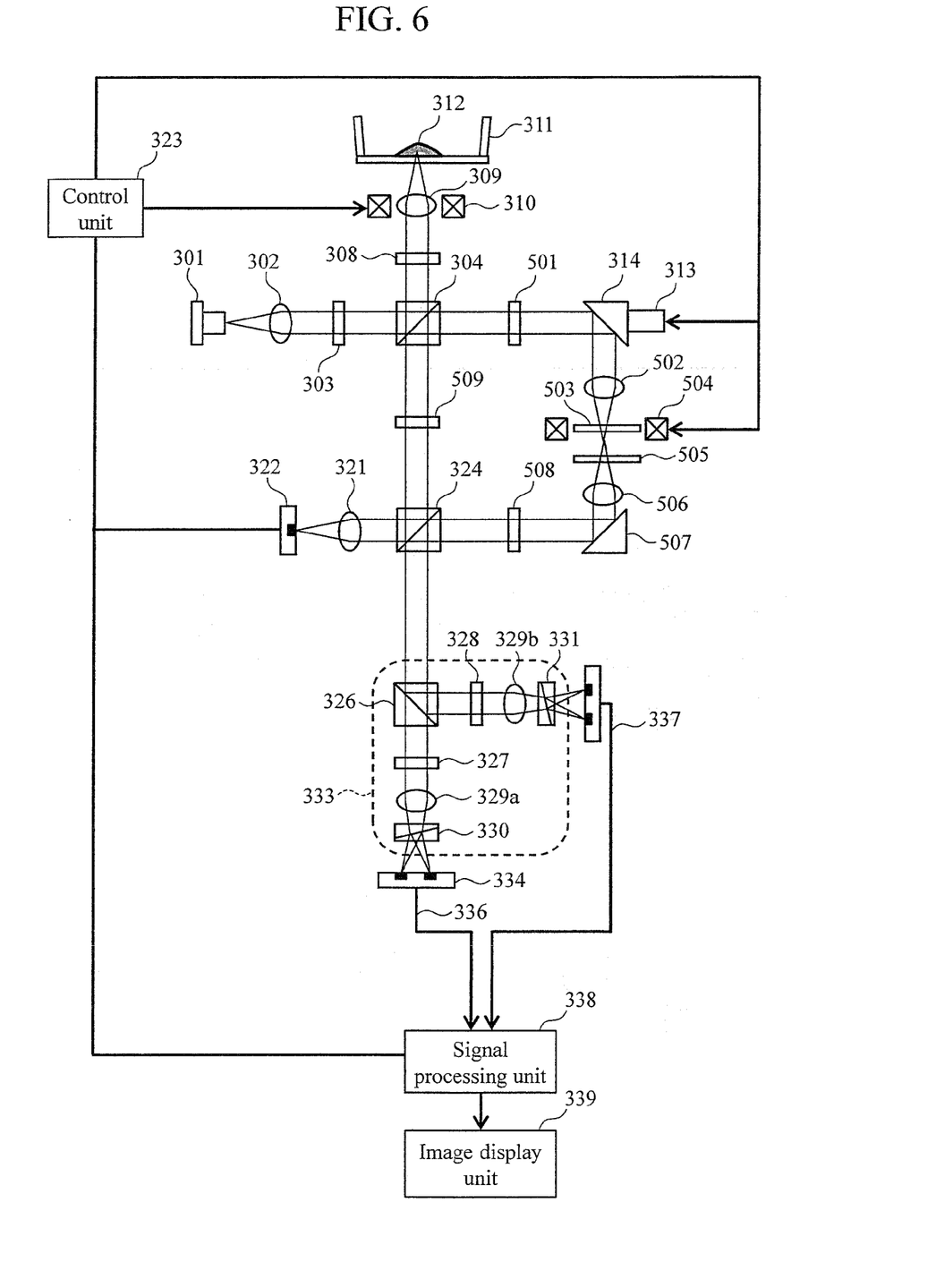
FIG. 6 is a schematic view showing an exemplary configuration of the optical measurement apparatus of the present invention.

FIG. 6 is a schematic view showing another embodiment of the optical measurement apparatus of the present invention. It should be noted that component parts that are identical to those shown in FIG. 3 are denoted by identical reference numerals, and detailed description thereof will be omitted. This embodiment differs from the first embodiment in the method of generating a control beam and the method of adjusting defocus of the control beam.

A laser beam is emitted from the light source 301. The laser beam is converted into a collimated beam by a collimator lens 302, and is subjected to polarization rotation by a λ/2 plate 303 capable of adjusting the optical axis direction, and is further split into two by a polarization beam splitter 304. One of the light beams split by the polarization beam splitter 304 passes through a λ/4 plate 308 at which the optical axis is set to about 22.5° with respect to the horizontal direction, as a signal beam, and thus is converted from the s-polarized beam into a circularly polarized beam. Then, the beam is focused onto and irradiates a target 312 to be measured, which is arranged in a sample container 311, by an objective lens 309 with a numerical aperture of greater than or equal to 0.4. Herein, the objective lens 309 is moved by an objective lens actuator 310 under the control of a control unit 323, so that the focus position (i.e., measurement position) of the signal beam is moved by the objective lens 309. A signal beam reflected or scattered by the target to be measured passes through the objective lens 309 again, and is then converted from the circularly polarized beam into a s-polarized beam by the λ/4 plate 308. Then, the beam becomes incident on the polarization beam splitter 304.

The other of the light beams split by the polarization beam splitter 304 passes through a λ/4 plate 501 at which the optical axis is set to about 22.5° with respect to the horizontal direction, as a reference beam, and thus is converted from the p-polarized beam into a circularly polarized beam. Then, the beam is reflected by a mirror 314 attached to a piezoelectric element 313. Then, the beam is focused by an objective lens 502 that is the same lens as the objective lens 309, and becomes incident on a plate 503 whose position in the optical axis direction is controlled by a flat plate actuator 504 and that is substantially transparent to a laser beam. The reference beam that has become incident on the flat plate 503 is partially reflected as a control beam from the rear surface of the flat plate 503 (when seen from the incident direction of a light beam), and is then reflected by the mirror 314 through the objective lens 502 again. Then, the beam is converted from the circularly polarized beam into a s-polarized beam by the λ/4 plate 501, and then becomes incident on the polarization beam splitter 304. Herein, the thickness and material of the flat plate 503 are set so that spherical aberrations of the control beam are equal to spherical aberrations of the reflected beam from the sample container (more precisely, the interface between the sample container 311 and the target 312 to be measured).

The control beam and the signal beam are combined by the polarization beam splitter 304. Then, the combined beam is subjected to polarization rotation by a λ/2 plate 509 capable of adjusting the optical axis direction, and is then split into two by a polarization beam splitter 324. One of the light beams split by the polarization beam splitter 324 is focused by a condenser lens 321 and is detected by a detector 322. The other of the light beams split by the polarization beam splitter 324 becomes a controlled signal beam.

Herein, the phase of the control beam is controlled by driving the piezoelectric element 313 with the control unit 323 such that the intensity of a light beam detected by the detector 322 becomes maximum. In addition, defocus of the control beam is controlled by driving the flat plate actuator 504 with the control unit 323 in synchronization with the objective lens actuator 310 such that the amount of defocus of the control beam becomes equal to that of the reflected beam from the bottom surface of the sample container 311 (to be more precise, the interface between the sample container 311 and the target 312 to be measured) contained in the signal beam. Further, spherical aberrations of the control beam are adjusted by the thickness and material of the flat plate 503 as described above.

The reference beam that has become incident on the flat plate 503 and passed through the flat plate 503 passes through a flat plate 505, and is converted into a collimated beam by an objective lens 506 that is the same lens as the objective lens 309. Then, the reference beam is reflected by a mirror 507, and is converted from the circularly polarized beam into a s-polarized beam by λ/4 plate 508 at which the optical axis is set to about −22.5° with respect to the horizontal direction. Herein, the thickness and material of a region of the flat plate 505 through which a light beam passes are equal to the thickness and material of a region of the flat plate 503 through which the light beam passes. Accordingly, spherical aberrations of the reference beam become equal to spherical aberrations of the signal beam, and thus, a decrease in the efficiency of interference between the signal beam and the reference beam can be avoided. The controlled signal beam and the reference beam are combined by the polarization beam splitter 324, whereby a combined beam is generated. The combined beam is guided toward interference optics 333 that include a half beam splitter 326, a λ/2 plate 327, a λ/4 plate 328, condenser lenses 329a and 329b, and Wollaston prisms 330 and 331. The subsequent operations are similar to those in Embodiment 1. Thus, description thereof will be omitted.

In this embodiment, a control beam is generated by a transmissive element (i.e., the flat plate 503). Thus, it is possible to clearly visualize the surface of the target to be measured or the structure of the target to be measured around the measurement target holding unit using optics that are simpler and more compact than the optics of Embodiment 1.

In this embodiment, the flat plate 503 for generating a control beam is inserted in the optical path of a reference beam. However, similar functions can also be implemented even when the flat plate 503 is inserted in the optical path of a signal beam. In such a case, the objective lenses 502 and 506, the flat plates 503 and 505, and the flat plate actuator 504 are inserted between the polarization beam splitter 304 and the λ/4 plate 308, and an element that controls the phase of a signal beam is inserted between the λ/4 plate 308 and the objective lens 309, so that a phase difference between the signal beam and the control beam is controlled.

In addition, in this embodiment, the thickness of a region of the flat plate 503 through which a light beam passes is set so that spherical aberrations that are imparted to the control beam by the flat plate 503 become equal to spherical aberrations that are imparted to the reflected beam from the sample container 311 by the sample container, whereby the efficiency of interference between the control beam and the reflected beam from the sample container improves. Accordingly, the reflected beam from the sample container can be cancelled out more precisely, and thus, the surface of the target to be measured or the structure of the target to be measured around the measurement target holding unit can be visualized more clearly.

[Embodiment 3]

Figure 7:
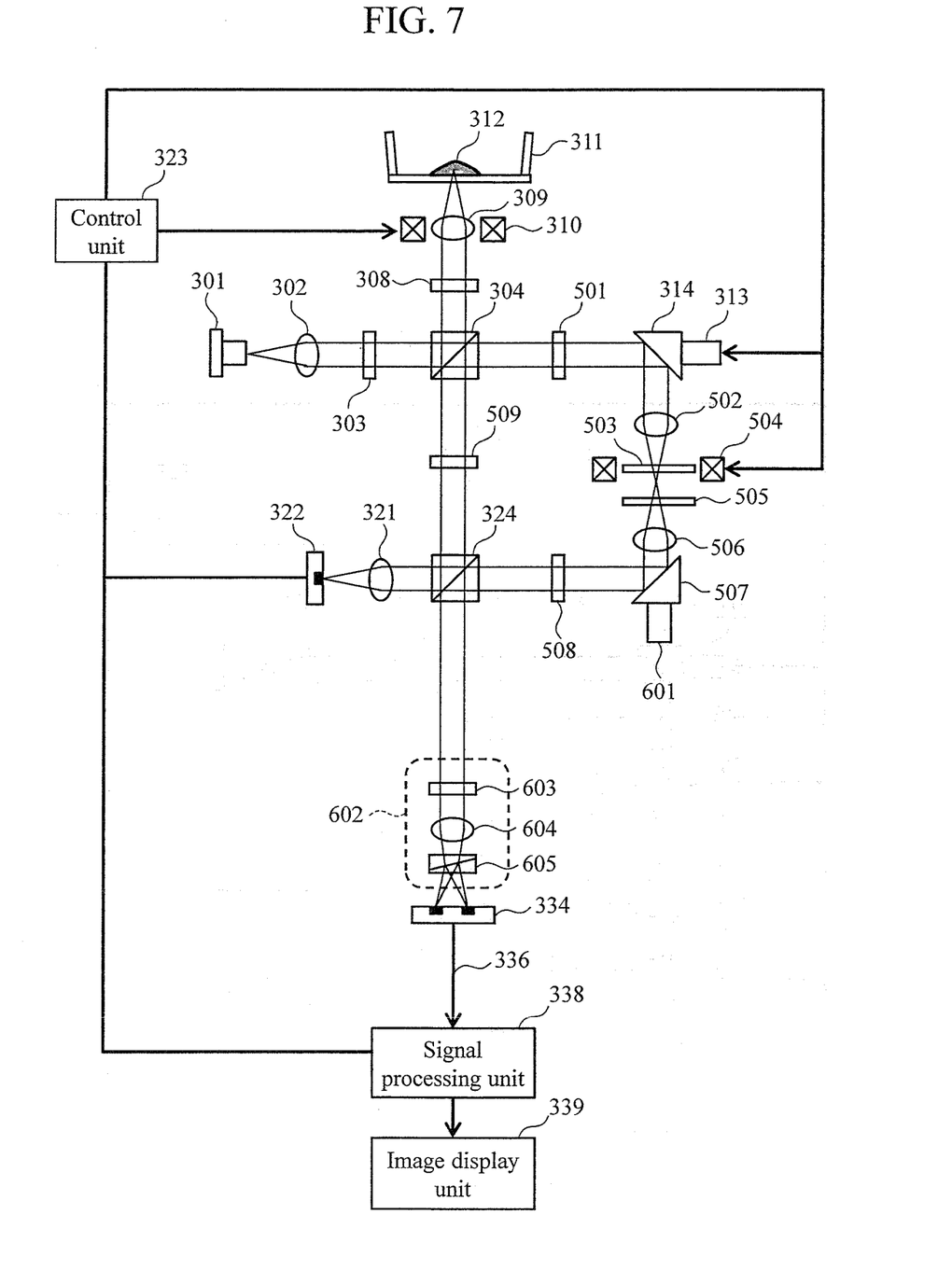
FIG. 7 is a schematic view showing an exemplary configuration of the optical measurement apparatus of the present invention.

FIG. 7 is a schematic view showing another embodiment of an optical measurement apparatus in accordance with the present invention. It should be noted that component parts that are identical to those shown in FIG. 3 are denoted by identical reference numerals, and detailed description thereof will be omitted. This embodiment differs from Embodiment 2 in that two interference beams are generated by interference optics, and a piezoelectric element for rapidly modulating the phase of a reference beam is used.

This embodiment is substantially similar to Embodiment 2 up to a configuration in which a laser beam is emitted from a light source 301 and a controlled signal beam is combined with a reference beam to generate a combined beam. However, this embodiment differs from Embodiment 2 in that a mirror 507 is mounted on a piezoelectric element 601 for rapidly modulating the phase of the reference beam. The combined beam is guided to interference optics 602 that include a λ/2 plate 603, a condenser lens 604, and a Wollaston prism 605. The combined beam that has become incident on the interference optics 602 passes through the λ/2 plate 603 at which the optical axis is set to about 22.5° with respect to the horizontal direction, and is focused by a condenser lens 604, and is further split into two by the Wollaston prism 605, whereby a first interference beam and a second interference beam having a phase difference of 180° are generated. The first interference beam and the second interference beam are detected by a current differential photodetector 334, whereby a signal 336 that is proportional to the intensity difference between the first interference beam and the second interference beam is output. The signal 336 is represented by the following formula.

$$I = 4\int_D |E'_{sig}||E_{ref}|\cos(\phi'_{sig} - \phi_{ref}) dr \qquad (19)$$

Figure 8:
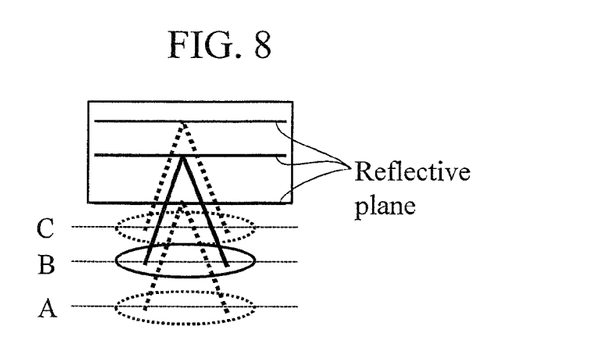
FIG. 8 is a schematic view showing a view in which an objective lens is moved in the optical-axis direction.
Figure 9:
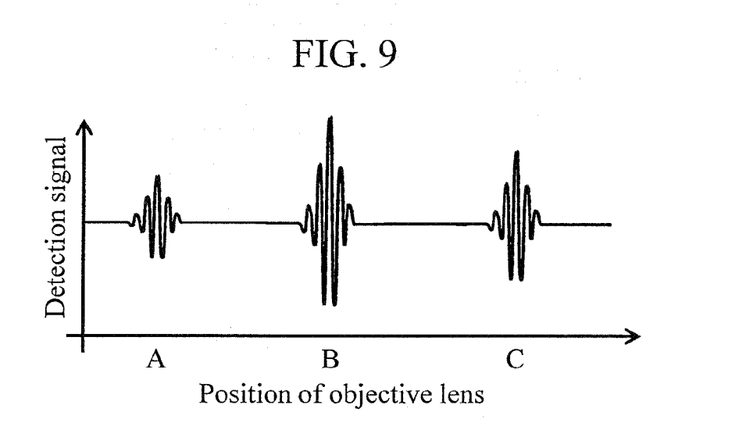
FIG. 9 is a schematic view of a signal when a piezoelectric element is not driven.
Figure 10:
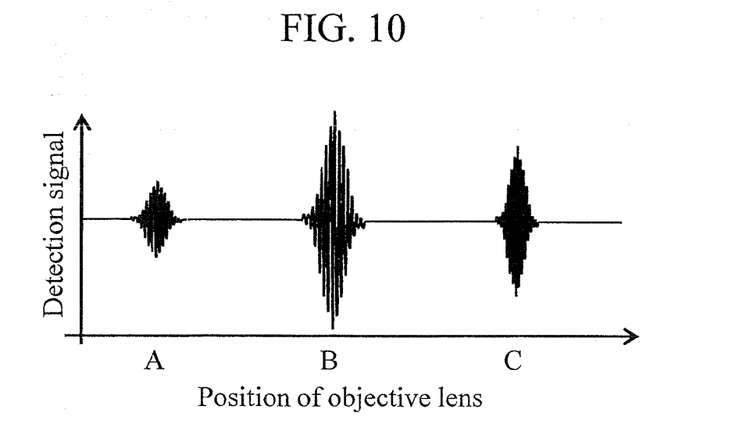
FIG. 10 is a schematic view of a signal when a piezoelectric element is driven.

In this embodiment, the piezoelectric element 601 is driven in acquisition of a signal, so that the phase of a reference beam is modulated more rapidly than a change in the phase of a signal beam that occurs while the objective lens 309 is moved. FIGS. 8 to 10 are diagrams illustrating signals that are detected when the objective lens 309 is moved in the z-direction using the OCT apparatus of this embodiment. Herein, FIGS. 9 and 10 show detection signals that are obtained when the target to be measured has three reflective planes as shown in FIG. 8.

FIG. 9 is a schematic view of a signal that is obtained when the piezoelectric element 601 is not driven. In such a case, the number of waves that are contained in an envelope of a signal from a reflective plane is approximately given by the (wavelength)/(peak width of the signal). The peak width of a signal is represented by $\lambda/NA^2$ where the wavelength of a laser beam is λ and the numerical aperture of the objective lens is NA. Thus, (wavelength)/(peak width of the signal)=$1/NA^2$. For example, when NA=0.6, the value is about 2.8. Thus, as the frequency of the envelope differs from the frequency of waves that are contained in the envelope only by about 2.8 times, it is difficult to apply envelope detection and thus generate image data on the basis of the detection signal. Meanwhile, when the piezoelectric element 601 is driven, a signal such as the one shown in FIG. 10 is obtained. In such a case, the phase of the reference beam is rapidly modulated while the focus position of the signal beam passes through the reflective plane. Thus, the number of waves that are contained in the envelope of a signal from a reflective plane increases in accordance with the speed of phase modulation. Thus, as the frequency of the envelope greatly differs from the frequency of waves that are contained in the envelope, it is possible to apply envelope detection and generate image data on the basis of the detection signal. That is, in this embodiment, a desired signal can be acquired from a detection signal through envelope detection unlike in Embodiment 2. Thus, functions that are similar to those in Embodiment 2 can be implemented with less detectors.

It should be noted that the present invention is not limited to the aforementioned embodiments, and includes a variety of variations. For example, although the aforementioned embodiments have been described in detail to clearly illustrate the present invention, the present invention need not include all of the structures described in the embodiments. It is possible to replace a part of a structure of an embodiment with a structure of another embodiment. In addition, it is also possible to add, to a structure of an embodiment, a structure of another embodiment. Further, it is also possible to, for a part of a structure of each embodiment, add/remove/substitute a structure of another embodiment.

REFERENCE SIGNS LIST

301 Light source
302 Collimator lens
303,306,319,327 λ/2 plate
304,307,320,324 Polarization beam splitter
308,315,328,501 λ/4 plate
309,316,502,506 Objective lens
310,317 Objective lens actuator
311 Sample container
312 Target to be measured
313 Piezoelectric element
314,325,507 Mirror
333 Interference optics
326 Half beam splitter
321,329 Condenser lens
330,331 Wollaston prism
334,335 Current differential photodetector
338 Signal processing unit
323 Control unit
339 Image display unit
318,503,506 Flat plate

What is claimed is:

1. An optical measurement apparatus comprising:
a light source configured to emit a laser beam;
at least one first optical splitter configured to split the laser beam into a reference beam and an other beam;
at least one second optical splitter configured to split the other beam into a signal beam and a control beam;
an objective lens configured to focus the signal beam onto a target to be measured and irradiate the target to be measured with the signal beam;
a first actuator configured to move a focus position of the signal beam;
a second actuator configured to control an amount of defocus of the control beam;
a optical phase modulator configured to control a phase difference between the control beam and the signal beam,
wherein the at least one second optical splitter is further configured to combine a signal beam reflected or scattered by the target to be measured with the control beam to generate a controlled signal beam;
interference optics configured to combine the controlled signal beam with the reference beam to generate a plurality of interference beams with different phases;
a photodetector configured to detect the interference beams;
a controller configured to control the first actuator, the second actuator, and the optical phase modulator.

2. The optical measurement apparatus according to claim 1, wherein the objective lens has a numerical aperture of greater than or equal to 0.4.

3. The optical measurement apparatus according to claim 1, further comprising at least one flat plate configured to impart a spherical aberration to the control beam.

4. The optical measurement apparatus according to claim 1, wherein the second actuator is configured to control an amount of defocus of the control beam so that the amount of defocus of the control beam becomes equal to that of a beam reflected by a surface of the target to be measured or by a holding unit that holds the target to be measured, the reflected beam being contained in the signal beam.

5. The optical measurement apparatus according to claim 1, wherein the second actuator controls the amount of defocus of the control beam so that, provided that a wavelength of the laser beam is λ and a numerical aperture of the objective lens is NA, a difference between the amount of defocus of the control beam and an amount of defocus of a beam reflected by a surface of the target to be measured or by a holding unit that holds the target to be measured is $0.856\lambda/(NA)^2$, the reflected beam being contained in the signal beam.

6. The optical measurement apparatus according to claim 1, further comprising a wave plate configured to adjust an intensity of the control beam contained in the controlled signal beam.

7. The optical measurement apparatus according to claim 1, wherein
the interference optics generate four interference beams,
an interference phase of the signal beam and the reference beam of each of the four interference beams differs from one another by an integral multiple of substantially 90°, and
pairs of interference beams are detected by a current differential detector, each pair having a difference of substantially 180° in the interference phase of the signal beam and the reference beam.

8. The optical measurement apparatus according to claim 1, further comprising a second optical phase modulator configured to modulate an optical path length difference between the signal beam and the reference beam more rapidly than a rate of change of an optical path length of the signal beam that occurs while the focus position of the signal beam is moved, wherein the interference optics are configured to generate two interference beams, and the interference beams are detected by a current differential photodetector.

9. An optical measurement apparatus comprising:
a light source configured to emit a laser beam;
at least one first optical splitter configured to split the laser beam into a signal beam and a reference beam;
at least one plate configured to partially reflect one of the signal beam or the reference beam as a control beam;
an objective lens configured to focus the signal beam onto a target to be measured and irradiate the target to be measured with the signal beam;
a first actuator configured to move a focus position of the signal beam;
a second actuator configured to control an amount of defocus of the control beam;
a optical phase modulator configured to control a phase difference between the control beam and the signal beam,
wherein the at least one first optical splitter is further configured to combine a signal beam reflected or scattered by the target to be measured with the control beam to generate a controlled signal beam;

interference optics configured to combine the controlled signal beam with the reference beam to generate a plurality of interference beams with different phases;

a photodetector configured to detect the interference beams;

a controller configured to control the first actuator, the second actuator, and the optical phase modulator.

10. The optical measurement apparatus according to claim 9, wherein the objective lens has a numerical aperture of greater than or equal to 0.4.

11. The optical measurement apparatus according to claim 9, wherein the at least one plate comprises at least one flat plate configured to impart a spherical aberration to the control beam.

12. The optical measurement apparatus according to claim 9, wherein the second actuator is configured to control an amount of defocus of the control beam so that the amount of defocus of the control beam becomes equal to that of a beam reflected by a surface of the target to be measured or by a holding unit that holds the target to be measured, the reflected beam being contained in the signal beam.

13. The optical measurement apparatus according to claim 9, wherein the second actuator controls the amount of defocus of the control beam so that, provided that a wavelength of the laser beam is $\lambda$ and a numerical aperture of the objective lens is NA, a difference between the amount of defocus of the control beam and an amount of defocus of a beam reflected by a surface of the target to be measured or by a holding unit that holds the target to be measured is $0.856\lambda/(NA)^2$, the reflected beam being contained in the signal beam.

14. The optical measurement apparatus according to claim 9, further comprising a wave plate configured to adjust an intensity of the control beam contained in the controlled signal beam.

15. The optical measurement apparatus according to claim 9, wherein
the interference optics generate four interference beams,
an interference phase of the signal beam and the reference beam of each of the four interference beams differs from one another by an integral multiple of substantially 90°, and
pairs of interference beams are detected by a current differential detector, each pair having a difference of substantially 180° in the interference phase of the signal beam and the reference beam.

16. The optical measurement apparatus according to claim 9, further comprising a second optical phase modulator configured to modulate an optical path length difference between the signal beam and the reference beam more rapidly than a rate of change of an optical path length of the signal beam that occurs while the focus position of the signal beam is moved, wherein the interference optics are configured to generate two interference beams, and the interference beams are detected by a current differential photodetector.

* * * * *